United States Patent [19]

Thoma

[11] 4,235,866

[45] Nov. 25, 1980

[54] PROCESS FOR THE TOTAL DETERMINATION OF HORMONES AND PHARMACEUTICALS

[75] Inventor: Hans A. Thoma, Munich, Fed. Rep. of Germany

[73] Assignee: Chandon Investment Planning Ltd., Grand Cayman, Cayman Islands

[21] Appl. No.: 899,742

[22] Filed: Apr. 24, 1978

[30] Foreign Application Priority Data

Apr. 27, 1977 [DE] Fed. Rep. of Germany ....... 2718700

[51] Int. Cl.$^2$ ..................... G01N 33/16; A61K 43/00
[52] U.S. Cl. ..................................... 424/1; 23/230 B; 424/12; 435/7; 435/35
[58] Field of Search ..................... 424/1, 12; 23/230 B; 195/103.5 A, 103.7

[56] References Cited

U.S. PATENT DOCUMENTS

| | | | |
|---|---|---|---|
| 3,962,039 | 6/1976 | Bates | 195/103.5 R |
| 4,061,466 | 12/1977 | Sjohölm et al. | 23/230 B |

OTHER PUBLICATIONS

Goodfriend et al., Immuno Chemistry, vol. 6, May, 1969, pp. 481–484.

Primary Examiner—Benjamin R. Padgett
Assistant Examiner—Christine M. Nucker
Attorney, Agent, or Firm—Schwartz, Jeffery, Schwaab, Mack, Blumenthal & Koch

[57] ABSTRACT

Disclosed is a method for the total determination of hormones and pharmaceuticals partially bound to specific or non-specific proteins, by the enzymatic hydrolysis of the bonding proteins, the reaction of the hormones or pharmaceuticals with an antibody and the radioimmunological determination of the hormones and pharmaceuticals, characterized by the fact that the immobilized antibodies are used.

3 Claims, No Drawings

PROCESS FOR THE TOTAL DETERMINATION OF HORMONES AND PHARMACEUTICALS

TECHNICAL FIELD OF THE INVENTION

The invention concerns a process for the total determination of hormones and pharmaceuticals. More specifically, the invention relates to the total determination of hormones or pharmaceuticals bonded partially to specific or non-specific bonding proteins by the enzymatic hydrolysis of the bonding proteins, the reaction of the hormones or pharmaceuticals with an antibody and the radioimmunological determination of hormones or pharmaceuticals.

BACKGROUND OF THE PRIOR ART

Various methods for the total determination of hormones or pharmaceuticals present in human serum, bonded partially to specific or non-specific bonding proteins, are known. In recent years, the relatively new radioimmunological techniques have contributed substantially to the exact determination of hormones.

Detailed descriptions of radioimmunoassays are found, for example, in Clinical Chemistry, Vol. 19, No. 2, 1973, p. 145. In Clinical Chemistry, Vol. 19, No. 12, 1973, p. 1339, and Clinical Chemistry, Vol. 21, No. 7, 1975, p. 829, radioimmunological techniques are described in which an antibody enclosed in a gel is used. The inclusion of the antibody in gel is considered advantageous by the authors, because in this manner interactions with molecules of high molecular weight are excluded. However, these known working processes are not intended for total hormone determination. Nevertheless, from a medical standpoint, total hormone determination is essential.

Methods of the total determination of hormones through the enzymatic hydrolysis of the bonding proteins and with radioimmunological techniques are known from J. Clin. Endocrinol. Metab. 42, 189, 1976 and Clinical Chemistry, Vol 22, No. 11, 1976, p. 1850. These articles show that enzymatic cleavage has significant advantages compared with methods used heretofore, such as, for example, solvent extraction and heat denaturation. Advantages specifically named are the facts that extraction with organic solvents and the chromatographic purification of samples are eliminated, that the time and expense of the determination is reduced, that scinitallation counting in the liquid is eliminated, that specificity and accuracy is improved, that the method of determination can be automated, and that the method is universally applicable.

However, the enzyme used to hydrolyze the bonding protein also attacks the antibody introduced in the next working step and destroys the latter. For this reason, the enzyme must be deactivated prior to the addition of said antibody. Inactivation of enzymatic activity is possible in a number of ways, for example, the enzyme can be denaturated by a substantial change in the pH value or by a heat effect.

However, this denaturization step is extremely disadvantageous. It requires either the addition of supplemental chemicals which introduces still more factors of interference in the system or it requires long periods of time for heat denaturization. The heat effect must last for approximately 5 minutes, while the cooling period amounts to approximately 15 minutes. This denaturization step thus represents a substantial hindrance in the automation of the determination. Further, depending on the system applied, specifically the enzyme used, different types of denaturization must be performed, which opposes the general applicability of the method of determination and its automation.

SUMMARY OF THE INVENTION

To avoid the difficulties of the prior art, the present invention creates a method for the total determination of hormones and pharmaceuticals in which no denaturing step is necessary. Thus, it is an object of the invention to render the method of determination universally applicable, to reduce the time and expense of the determination and to make possible the automation of the determination.

According to the invention, the object is attained by a method for the total determination of hormones and pharmaceuticals partially bound to specific or non-specific proteins, by the enzymatic hydrolysis of the bonding proteins, the reaction of said hormones or pharmaceuticals with an antibody and the radioimmunological determination of the hormones and pharmaceuticals, characterized by the fact that immobilized antibodies are used.

The antibody is preferably enclosed in a polymer gel. Acrylamide polymers and acrylamide copolymers are particularly preferred as the polymer gel. Specific advantages of copolymers are described in greater detail in Applicant's related application.

The application of immobilized antibodies protects the antibodies from the enzyme. The antibodies are included in the polymer matrix which the enzyme, because of its size, cannot penetrate. As a result of this simple and elegant measure in the process of the invention, the step of denaturing the enzyme may be eliminated. The process thus involves significantly less labor and requires less time. The method is universally applicable to different systems, because the specific enzyme denaturization is eliminated. Furthermore, the process of the invention is of particular importance, as it lends itself especially well to the automation of the determination.

DETAILED DESCRIPTION OF THE INVENTION

The method of the invention is suitable for the determination of different hormones and pharmaceuticals, which are present in the serum or the plasma in a state bound in part to specific or non-specific bonding proteins. The hormones to be determined are thyroid hormones, particularly thyroxine and tri-iodothyroxin, the steroid hormones such as cortisol, testosterone, progesterone, estron, estradiol and estriol and the heart glycosides, such as digitoxin and digoxin. Further, vitamins, particularly Vitamin B12 and folic acid, as well as pharmaceuticals with strong protein bonds, such as, for example, anti-coagulants, dicumarol, analgetics and salycilates, may be determined.

In the execution of the determination, the serum or plasma containing the hormone or pharmaceutical is placed in contact with a solution of an enzyme, the enzyme hydrolytically cleaving the bonding protein. The choice of the enzyme is directed by the specific bonding protein. For example, the following enzymes may be used depending on the system: aminopeptidase, bromelin, carboxypeptidase, chymotripsin, elastase, ficin, leucinaminopeptidase, lipase, pancreatin, papin, pepsin, pronase, protease, proteunase, thermolysin and trypsin. For the determination of hormones such as thyroxin and cortisol, proteolytic enzymes such as proteinase, pronase or pepsin are particularly suitable.

The reaction of the sample with enzymatic solution can be performed on a controlled temperature means at temperatures around 35° C. or a room temperature. The period of time required for the enzymatic hydrolysis of the protein depends on the enzyme used and is between 15 minutes and 4 hours, in many cases between 15 and 30 minutes.

Following the hydrolysis of the protein, the sample is mixed with a marked indicator haptene and added to the immobilized antibody.

The addition is effected with the aid of a multichannel piston pump. With the pump running in reverse, the reaction mixture is suctioned quantitatively into small columns, said columns containing the immobilized antibody. An especially suitable apparatus for this is described in Applicant's copending application 899,710, filed Apr. 24, 1978.

Subsequently, a rest interval is provided for the reaction of the marked and unmarked substance to be determined with the immobilized antibody.

A final extraction with water or a buffer solution yields the separation of haptene bound to the antibody and the free haptene. The residual radioactivity in the extract or the column is a measure of the concentration of the substance to be determined. The radioimmunological principle is known, for example, from D. S. Skelley et al, *Clinical Chemistry*, Vol. 19, No. 2, 1973, p. 146ff.

Alternative methods of determination, such as fluoroimmunological determination or determination by enzymatic marking, may also be used.

The synthesis of antigens, the production of antisera, for example, through the immunication of rabbits and the isolation and immobilization of antibodies, are known (see for example, D. S. Skelley et al., *Clinical Chemistry*, Vol. 19, No. 2, 1973, p. 146ff.

Immobilized antibodies are produced, for example, by adding a solution of the antibody to a monomer mixture. The mixture is subjected to conditions of free radical polymerization and the polymer obtained is comminuted, washed and dried. Acrylamide is particularly suitable as the monomer. By copolymerizing the acrylamide with acryl derivatives with different functional groups, such as, for example, acrylic acid, methacrylic acid and methacrylamide, advantageous variations of the matrix may be obtained. Through the addition of copolymers, particularly the hydrophobicity and the charge of the matrix, can be affected and thus, the reaction of the antibody with the hormone or pharmaceutical to be determined, influenced.

In order to obtain a suitable pore size of the polymer matrix, the monomer concentration is varied. A monomer concentration in the range of about 20% results in a pore size of about 7 to 10 Å.

The use of an ion-exchanged polymer matrix is also advantageous. The buffer action obtained by the ion exchange can be used to alter the pH values in the sample to be determined. An advantageous system is, for example, a copolymer of acrylamide and 20 to 60% acrylic acid and/or methacrylic acid, prepared from an approximately 20% monomer solution in which at least part of the acid groups are converted into the corresponding alkali or alkaline earth salts.

The invention will be explained hereafter in more detail with the aid of examples.

EXAMPLE 1

Determination of Thyroxin by Enzymatic Hydrolysis with Pronase

The antigen synthesis was performed beginning with thyroxine ethyl ester and coupling on albumin with carbodiimide. The antibody was produced through the immunization of rabbits.

The antibody was then enclosed in polymer gel. An acrylamide monomer with a concentration of 2.9 mole/l was used. For the initial mixture, 5 g acrylamide and 1.25 g N,N'-methylene-bis-acrylamide were dissolved in a beaker in 24 ml of a phosphate buffer with a pH value of 7.2. Following the admixture of the antiserum in 1 ml phosphate buffer, the reaction was started with 0.15 g riboflavin and 0.10 ml N,N,N',N'-tetramethylethylenediamine and irradiated with UV light. During the irradiation period of 45 minutes the temperature was maintained at less than 50° C. The gel block was subsequently comminuted, washed with distilled water, and dried.

The zero serum was produced by reacting 1 ml serum and a pronase solution with a concentration of 2 mg/ml for 30 minutes at 35° C. Subsequently, 2 g of an ion exchange resin (Amberlite 400) were added.

After this, 50 $\mu$l of the zero serum with a content of 18 g thyroxine per 100 ml were reacted with 350 $\mu$l enzyme solution with a concentration of 2 mg per ml for 30 minutes at a temperature of 35° C.

To 100 $\mu$l of this solution, 700 $\mu$l of the tracer solution with a content of 5.2 ng/ml of radioactive marked thyroxine and 50 $\mu$l buffer solution with a pH value of 7.2 were added. 350 $\mu$l of this solution were added to 60 mg of the antibody gel. The incubation period was 30 minutes, the temperature 22° C. Subsequently, the solution was extracted for 5 minutes with a pumping rate of 0.5 ml/min.

A dose effect curve for thyroxine was established with thyroxine solutions having concentrations of 5 ng, 10 ng, 20 ng and 50 ng per 100 ml. These solutions were reacted with 350 $\mu$l enzyme solution (concentration 2 mg/ml) for 30 minutes at a temperature of 35° C.

To the 100 $\mu$l of this solution, 700 $\mu$l tracer solution (5.2 ng/ml) and in place of the buffer, 50 $\mu$l zero serum were added.

The evaluation resulted in a recovery of 99%.

EXAMPLE 2

Total Determination of Thyroxine by Enzymatic Hydrolysis with Proteinase

The working procedure of Example 1 was followed, but instead of the pronase solution, a proteinase solution with a concentration of 2 mg/ml was used.

The serum applied consisted of a zero serum with a content of 6 mg per 100 ml.

The recovery was 98.5%.

EXAMPLE 3

Total Determination of Cortisol by Enzymatic Hydrolysis with Pronase

The procedure of Example 1 was followed, but a serum containing 18 $\mu$g cortisol per 100 ml was used. As the tracer solution, a solution of radioactive marked cortisol in a concentration of 0.15 ng/ml was used. The antibody used was prepared by the synthesis of cortisol-C3-oxime and coupling at albumin with mixed anhydride and antibody production through the immunication of rabbits.

The recovery was 97%.

EXAMPLE 4

Total Determination of Cortisol by Enzymatic Hydrolysis with Proteinase

The working procedure of Example 3 was followed, but the serum contained 6 μg cortisol per 100 ml and a proteinase solution with a concentration of 2 mg/ml was used.

The antibody applied in Example 4 was the same as the antibody of Example 3.

The recovery was 98%.

EXAMPLE 5

Total Determination of Thyroxine by Enzymatic Hydrolysis with Pepsin

The general working procedure of Example 1 was followed.

10 μl serum with a content of 18 μg thyroxine per 100 ml were mixed with 160 μl of an enzyme solution, which consisted of 2 mg/ml pepsin dissolved in 0.1 n hydrochloric acid. The reaction with the enzyme was performed at room temperature for 30 minutes.

To this 170 μl subsequently 150 μl tracer solution with a content of 5.2 ng/ml of radioactive marked thyroxine were added.

The entire solution was then added to 60 mg of an antibody gel. The polymer matrix of the antibody gel consisted of a copolymer of acrylamide and 40 mole % of the sodium salt of methacrylic acid, prepared from a 20% monomer solution.

The incubation time was 30 minutes, the temperature 22° C.

An extraction followed for 5 minutes at a pumping rate of 0.5 ml/min.

The evaluation showed a recovery of 98%.

What is claimed is:

1. A process for the total determination of hormones and pharmaceuticals bonded partially to specific or non-specific bonding proteins comprising treatment of said bonded hormones and/or pharmaceuticals with an active enzyme to hydrolyze the bonding proteins, reaction of the hormones or pharmaceuticals in the presence of active enzyme with an immobilized antibody and radioimmunological determination of the hormones or pharmaceuticals.

2. The process of claim 1, wherein the antibodies are enclosed in a polymer gel.

3. The process of claim 1 or 2, wherein the antibodies are enclosed in an acrylamide polymer or acrylamide copolymer.

* * * * *